(12) United States Patent
Sanders et al.

(10) Patent No.: US 7,893,402 B2
(45) Date of Patent: Feb. 22, 2011

(54) MEASUREMENT OF THE MOBILITY OF MASS-SELECTED IONS

(75) Inventors: Ian Sanders, Brighton (GB); Gökhan Baykut, Bremen (DE); Jochen Franzen, Bremen (DE)

(73) Assignee: Bruker Daltonik GmbH, Bremen (DE)

( * ) Notice: Subject to any disclaimer, the term of this patent is extended or adjusted under 35 U.S.C. 154(b) by 245 days.

(21) Appl. No.: 12/052,267

(22) Filed: Mar. 20, 2008

(65) Prior Publication Data

US 2008/0251712 A1  Oct. 16, 2008

(30) Foreign Application Priority Data

Apr. 11, 2007 (DE) .................. 10 2007 017 055

(51) Int. Cl.
*B01D 59/44* (2006.01)
(52) U.S. Cl. .................. 250/290; 250/281; 250/282; 250/284; 250/288; 250/292
(58) Field of Classification Search .................. None
See application file for complete search history.

(56) References Cited

U.S. PATENT DOCUMENTS

| | | | |
|---|---|---|---|
| 5,572,035 A | 11/1996 | Franzen | |
| 5,905,258 A | 5/1999 | Clemmer et al. | |
| 6,323,482 B1 * | 11/2001 | Clemmer et al. | 250/287 |
| 6,498,342 B1 * | 12/2002 | Clemmer | 250/287 |
| 6,630,662 B1 | 10/2003 | Loboda | |
| 6,872,939 B2 | 3/2005 | Bateman et al. | |
| 6,960,761 B2 | 11/2005 | Clemmer | |
| 7,456,394 B2 * | 11/2008 | Cameron et al. | 250/288 |
| 7,569,812 B1 * | 8/2009 | Karpetsky et al. | 250/282 |
| 7,608,818 B2 * | 10/2009 | Miller et al. | 250/288 |
| 2008/0251712 A1 * | 10/2008 | Sanders et al. | 250/282 |
| 2009/0272891 A1 * | 11/2009 | Giles | 250/282 |

FOREIGN PATENT DOCUMENTS

| | | |
|---|---|---|
| GB | 2 421 843 A | 7/2006 |
| WO | WO 03/105183 A1 | 12/2003 |

* cited by examiner

*Primary Examiner*—David A Vanore
(74) *Attorney, Agent, or Firm*—Law Offices of Paul E Kudirka

(57) ABSTRACT

The mobility of mass-selected ions in gases is measured at pressures of a few hectopascal by selecting the ions under investigation in a quadrupole filter according to their mass-to-charge ratio m/z, measuring their mobility in a drift region at a pressure of a few hundred Pascal under the influence of a DC electric field and then filtering the measured ions by means of a quadrupole field in order to eliminate, or detect changes in, the mass-to-charge ratio. Several embodiments for the drift region are disclosed, in which the ions are kept in the axis of the drift region by RF fields. As these drift regions can also be utilized for a collision-induced decomposition of the ions, the device can additionally be used as a so-called triple quadrupole mass spectrometer.

10 Claims, 5 Drawing Sheets

MEASUREMENT OF THE MOBILITY OF MASS-SELECTED IONS

BACKGROUND

The invention relates to methods for measuring the mobility of mass-selected ions in gases at pressures of a few hectopascal and further relates to the corresponding apparatus. The ionization of dissolved substances by electrospray ionization (ESI) and the ionization of solid substances by matrix-assisted laser desorption (MALDI) have considerably advanced mass spectrometry with respect to the investigation of both small molecules and large biopolymers. In biochemistry, knowledge of the sequence of polymers is particularly important information for the characterization of proteins; in other words, knowledge of the sequence of amino acids. The amino acid sequences form the primary structure of the proteins. Yet the physiological activities and effects of proteins do not depend solely on the sequence. Chains of proteins form so-called secondary structures, such as alpha helices and beta sheets, and these undergo further folding to form tertiary structures, said structures frequently being able to assume several stable configurations. In many cases, these folding structures join together to form complexes and create so-called quaternary structures: hemoglobin, for example, is a characteristic tetramer with two alpha and two beta chains.

Recent investigations into proteins show that neurodegenerative diseases such as Alzheimer's, Parkinson's, Huntington's, ALS (amyotrophic lateral sclerosis), BSE (bovine spongiform encephalopathy) and the related Creutzfeldt-Jakob disease (CJD) are connected with protein misfolding. When investigating the different types of activity of the proteins, it is therefore also very important to obtain information on their folding structures. This information is often equally as important as the information concerning the amino acid sequence. If molecules with the same primary structure possess different folding forms, they are also called "conformation isomers".

Proteins with different folding structures which are introduced to an organism from outside often produce very different physiological effects. One folding form can have a toxic effect, while another can heal a disease. In the production of pharmaceuticals containing proteins, the quality control used must therefore also include the investigation of the folding structure. It is important to use a method with a large dynamic range of measurement to enable even very small contaminations with toxic substances to be identified.

Geometric changes of the proteins can also be brought about by posttranslational modifications (PTM). Approximately 70 percent of all proteins in the human body are glycosylated. A protein that is modified by polar groups such as phosphates or sugars can undergo structural rearrangements of the main body without losing stability in the process. Posttranslational modifications change the molecular weight of the proteins; phosphorylized or glycosylated proteins have geometric forms which are different to those of their unmodified analogs. Depending on the attachment point of the posttranslational modification, the protein will assume different geometric shapes even though they have the same mass, i.e., the protein will be folded differently. These different types of molecule having the same molecular formula and the same mass but a different primary structure are called "structural isomers".

Isomers of the primary structure (structural isomers) and isomers of the secondary or tertiary structure (conformation isomers) possess different geometric forms but exactly the same mass. Mass spectrometry is therefore unable to differentiate between them. One of the most efficient methods of identifying and separating such isomers is to separate them by their ion mobility. A cell for the measurement of ion mobility contains an inert gas (such as helium). The ions of the substance under investigation are pulled through the gas by means of an electric field. The high number of collisions with the gas molecules results in a constant drift velocity for each ionic species, which is proportional to the electric field intensity. The proportionality constant is called "ion mobility". The ion mobility is a function of the temperature, gas pressure, ion charge and, in particular, the collision cross-section. Isomeric ions of the same mass but different collision cross-sections possess different ion mobilities. Isomers with the smallest geometry possess the greatest mobility and therefore the highest drift velocity through the gas. Protein ions in the unfolded state undergo more collisions than tightly folded proteins. Unfolded protein ions therefore arrive at the end of the cell later than folded ions of the same mass.

A variety of information can be obtained from measurements of ion mobility. Simple measurements of relative ion mobility are frequently used to investigate changes in conformation or simply to discover the co-existence of different isomeric structures. Ions with the same mass-to-charge ratio m/z but different folding can be separated from each other relatively easily. It is also possible to determine absolute values for the collision cross-sections (with the extra effort of a calibration). Using the absolute values of the collision cross-sections in a given gas (such as helium) special computer programs can be used to distinguish between different possible folding structures. Such computer programs have become known as AMBER (Assisted Model Building and Energy Refinement) or CHARMM (Chemistry at HARvard Macromolecular Mechanics).

In chemical and biological research, it has become more important to know about the mobility of ions, and therefore devices for the measurement of ion mobility have been incorporated into mass spectrometers in order to combine the measurement of the mass-to-charge ratios of ions with the measurement of collision cross-sections.

The investigation of mass-selected ions with respect to isomeric compounds essentially requires an instrument containing the following components: (1) an ion source, (2) a mass spectrometric ion selector, (3) a measuring cell for the mobility measurement and (4) a time-resolving ion detector.

Often, a separation system for the separation of substances, such as a liquid chromatograph, is additionally used, particularly in conjunction with an electrospray ion source. Selected ions of the same mass are investigated with respect to their mobility; isomers with different mobility then still have the same mass. Therefore, after measuring the mobility, no further mass determination is normally necessary. An ion detector which can measure the ions of different mobilities by temporally resolving the ion current is therefore perfectly satisfactory.

Experiments show, however, that ions can also dissociate in the mobility measuring cell. The mixtures of ions or ion complexes which are of interest for an analysis of the ion mobility often contain quite unstable ions. In this case, not only the intact isomers leave the mobility measuring cell, but also ionized fragmentation products or dissociated ions from complexes, which will normally have different mobilities. Therefore, without a mass spectrometric analysis of the ions after they leave the mobility measuring cell it is not possible to make any statement about the presence of isomers of the mass-selected ions because the occurrence of a number of mobility signals does not permit any conclusion to be drawn about the mass of the ions causing these signals.

U.S. Pat. No. 6,630,662 (A. V. Loboda) discloses an arrangement where the mass filter is located downstream of the mobility measuring cell instead of upstream. The detector then only measures ions with the same mass-to-charge ratio. There could, however, be a fragment ion of a heavier ion with the same mass; this arrangement therefore offers no remedy. Furthermore, this patent specification introduces a moving gas in the mobility measuring cell, which produces a virtual shortening of the measuring cell. Additionally, the ions in the mobility cell are kept on axis by RF-generated pseudopotentials.

This patent also describes an arrangement in which the isomers are subsequently analyzed in a high-resolution time-of-flight mass spectrometer with orthogonal ion injection with the aim of obtaining complete mass spectra of the ion mixtures. Several patents have been elucidated in recent years in relation to this principle of combining the mobility measuring cells with high-resolution time-of-flight mass spectrometers, for example U.S. Pat. No. 5,905,258 (David E. Clemmer and James P. Reilly) and U.S. Pat. No. 6,960,761 (David E. Clemmer). They also describe combinations using time-of-flight mass spectrometers.

Such combinations of mobility measuring cells with orthogonal time-of-flight mass spectrometers (or other kinds of mass spectrometer) raise some problems, however, when the requirement is not just to filter out individual ionic species but to scan whole mass spectra. Time-of-flight mass spectrometers either use ion storage devices before the injection into the time-of-flight mass spectrometer, which destroys the mobility measurement, or they require a continuous ion current, which is not provided by mobility measuring cells. The ion signal of an isomer from an ion mobility measuring cell has a width of only a few hundred microseconds; this is not sufficient time to scan enough mass spectra for a good-quality sum spectrum.

Other types of mass spectrometer, such as ion cyclotron resonance mass spectrometers or RF ion traps, are even less suitable as analyzers for the composition of ions emerging from a mobility measuring cell. The temporal profiles of the signals from the mobility cells are not compatible with the requirements of the mass spectrometers with respect to the temporal duration of the applied ion currents. The only possibility is to collect only particular signals from the mobility cells with a temporal masking and to then subject them to a mass spectrometric analysis. This procedure, however, is not very effective and hardly justifies the development of the complex instrument it requires.

With such instruments, which consist of only a mass filter and an ion mobility measuring cell, the problem remains that the signals from isomeric molecular ions cannot be distinguished from fragment ions or reactively produced ions.

SUMMARY

In accordance with the principles of the invention, a method for measuring ion mobilities comprises the steps of selecting the ions according to their mass in a first mass filter, periodically collecting ions of the same mass over predetermined sampling times in small clouds, then separating these clouds of ions according to the mobility of their ions by switching potential gradient profiles in a drift region which is filled with a low pressure collision gas and then removing ions of unwanted masses in a second mass filter, before feeding them, time-resolved, to an ion detector. In one embodiment, quadrupole mass filters are used.

In another embodiment, the mass spectrometric instrument used for the inventive method comprises (a) an ion source, (b) a first mass filter, (c) a measuring cell to measure the mobility of ions in a collision gas under the influence of an electric field, (d) a second mass filter, and (e) an ion detector.

In other embodiments, in order to produce the pressure differentials between the drift region, which is operated at a few hectopascal for measuring the ion mobility, and the two quadrupole mass filters, which require a vacuum of better than 0.01 Pascal, ion guides with gas permeable electrode structures can be interposed, which are each equipped at both ends with lens systems with a small through-opening to impede the gas flow. The mass filters, the ion guides and the drift region are equipped with differentially operating turbomolecular and rotary pumps. Some (or all) of these pumps can be put together to form a combination pump.

In still other embodiments, the drift region can be arranged so that the ions are kept together on axis radially by pseudopotentials and are axially guided by real electrostatic potentials. The pseudopotentials can be generated by inhomogeneous RF fields (see for instance U.S. Pat. No. 5,572,035 A, J. Franzen); for this, quadrupole systems consisting of specially shaped single diaphragms, or parallel wires, other radially focusing drift regions formed from ring electrodes or from resistance wires wound as double or even quadruple helices can be used. This type of apparatus using two quadrupole mass filters and collisional focusing in the pseudopotential of the drift region can also be used as a daughter ion spectrometer or reaction product spectrometer if the drift region is used as collision chamber for the fragmentation or as reaction chamber.

It yet another embodiment, it is particularly favorable if the drift region can be subdivided into two sections in which different potential gradients can be set. It is then possible to create a potential minimum, in which the ions can initially be collected in the form of an ion cloud before being split up into several clouds in the drift region according to their mobility, by switching the potential gradient profiles.

The drift regions can be operated with either stationary or flowing gas. In the case of drift regions with flowing gas, there are particularly favorable forms of the drift cell and also of operating modes with a stationary separation of the ions of different mobility.

DETAILED DESCRIPTION

While the invention has been shown and described with reference to a number of embodiments thereof, it will be recognized by those skilled in the art that various changes in form and detail may be made herein without departing from the spirit and scope of the invention as defined by the appended claims.

Since many of the ions and ion complexes under investigation are very unstable, all undesirable fragment ions and undesirable decomplexation ions which are produced in the drift region (59), either during the process of introducing the ions or during their separation according to their mobility, may be filtered out, according to the invention, by a second mass filter (63). Ions produced by reactions with substances in the collision gas of the drift region, for example by reactions with impurities of the collision gas, may also be filtered out in this way. In these cases, the second mass filter (63) is set to allow the passage of ions of the same mass-to-charge ratio range as the first mass filter (55), thus permitting the mobilities of the selected ionic species to be measured without interferences. The mass range selected for the filtering is, as a rule, very narrow; usually it contains only the ions of one isotopic group. However, the second mass filter (63) can also be set to a different mass range in order to specifically measure fragmentations of the ions or reactions of the ions, possibly including their mobilities. In particular, the second mass filter (63) can also be operated without DC voltages, using only RF voltages, allowing all ions to pass through, and thus making it possible to determine whether, and how many of, the ions decompose, something which is not possible with a measurement with filtering.

Figure 1:
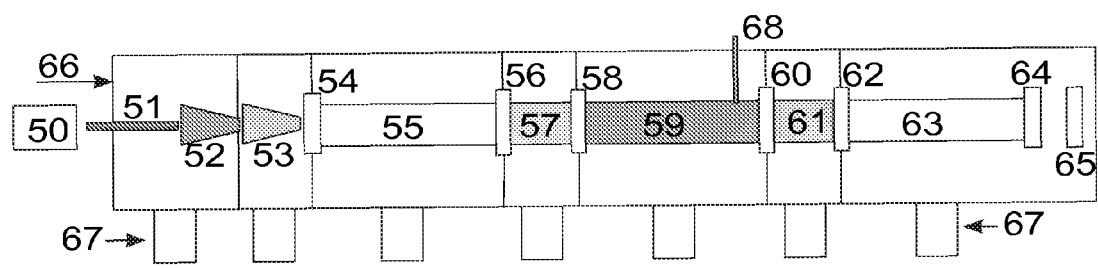
FIG. 1 is a schematic representation of a spectrometer for measuring the mobility of mass-selected ions according to this invention; the drift region (59) for measuring the ion mobility is arranged between two quadrupole mass filters (55, 63). The ions generated in the ion source (50) are introduced into the vacuum housing (66) via an inlet capillary (51) and then guided through two ion funnels (52, 53) to the first quadrupole mass filter (55). The lens systems (54, 56, 58, 60, 62 and 64) are responsible for the subsequent transfer and, if applicable, acceleration of the ions into the next stage; at the same time, they serve to separate to a large extent the individual stages with respect to their vacuum requirements. The two ion guides (57, 61) are interposed to allow differential pumping by the pumps (67), because, in the drift region, a pressure of several hectopascal is maintained by the gas feed (68), while the quadrupole filters (55) and (63) both need to be operated at a vacuum below 0.01 Pascal. The arrival time of the ions is measured in the ion detector (65). An optimum pressure for the measurement of ion mobilities is between approximately one and ten Pascal.
Figure 11:
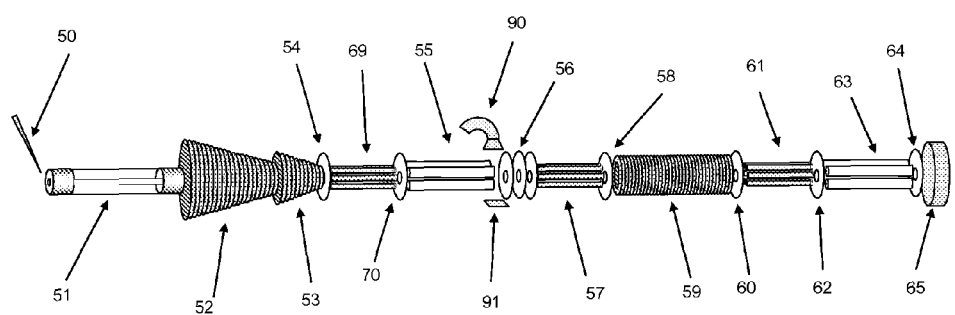
FIG. 11 shows the mass spectrometric instrument according to the invention in accordance with another embodiment. This arrangement is similar to that shown in FIG. 1 and elements with the same numerals as those in FIG. 1 perform the same functions. In the embodiment shown in FIG. 11, a further ion guide (69) with lens (70) is placed before the first quadrupole filter (59). Additionally, a detector (90) with deflection plate (91) is placed behind the first mass filter to enable the acquisition of mass spectra by scanning.

The combination of two quadrupole mass filters and an ion mobility spectrometer, according to the invention is schematically shown in FIGS. 1 and 11. The drift region (59) for measuring the ion mobility is located between the two quadrupole mass filters (55) and (63).

Ions are generated in an ion source (50) outside the vacuum system and introduced into the vacuum housing (66, FIG. 1; not shown in FIG. 11) through an inlet capillary (51). The vacuum housing is divided into many compartments with different residual pressures, which are differentially evacuated by a number of pumps (67, FIG. 1; not shown in FIG. 11). The ions are moved through the individual compartments, usually by the action of lens systems (54, 56, 58, 60, 62 and 64), which separate the compartments ion optically and with respect to vacuum requirements. The lens systems are responsible for the subsequent transfer and, if applicable, acceleration of the ions into the next compartment. At first, the ions are guided through two ion funnels (52, 53) to the first quadrupole mass filter (55), where all ions under investigation pass through and all other ions are filtered out. The ions selected are transferred into the drift region (59) of the ion mobility spectrometer by a gas-permeable ion guide (57), because the quadrupole filter (55) requires a pressure below 0.01 Pascal, whereas in the drift region a pressure of several hundred Pascal must be maintained. The gas-permeable ion guide (57) allows differential pumping.

The measurement of the ion mobility in the drift region (59), usually but not in all embodiments operated by ion pulses, is explained in more detail below for the different embodiments of these drift regions. The ions of different mobility which exit the drift region (59) in time sequence are fed via a further ion guide (61), which largely removes the accompanying collision gas, then through the second quadrupole filter (63) to the ion detector (65). As explained above, the two ion guides (57, 61) are interposed to allow differential pumping by the pumps (67, FIG. 1), because the pressure in the drift region (59) needs to be about 4 orders of magnitude higher than the pressure in the quadrupole filters (55) and (63).

The arrival time of the ions is measured in the ion detector (65). This produces a mobility spectrum of the ions in every measurement period of the ion mobility spectrometer, from which it is possible to identify, for example, different folding states of the protein ions. Consecutive mobility spectra can be added together because the quality of the spectra improves when higher numbers of ions are measured.

Experiments have already been successfully carried out in different laboratories to calculate the folding states of ions from their mobility, the starting point in most cases being a theoretical calculation of the different possible folding states. For this kind of determination, the potential gradient, type of gas, gas velocity and gas pressure must be very accurately known and need to be controllable; a careful calibration is also necessary, requiring reference substances with known collision cross-sections.

Several possible embodiments and modes of operation for the drift region of the ion mobility spectrometer are presented here.

Figure 2:
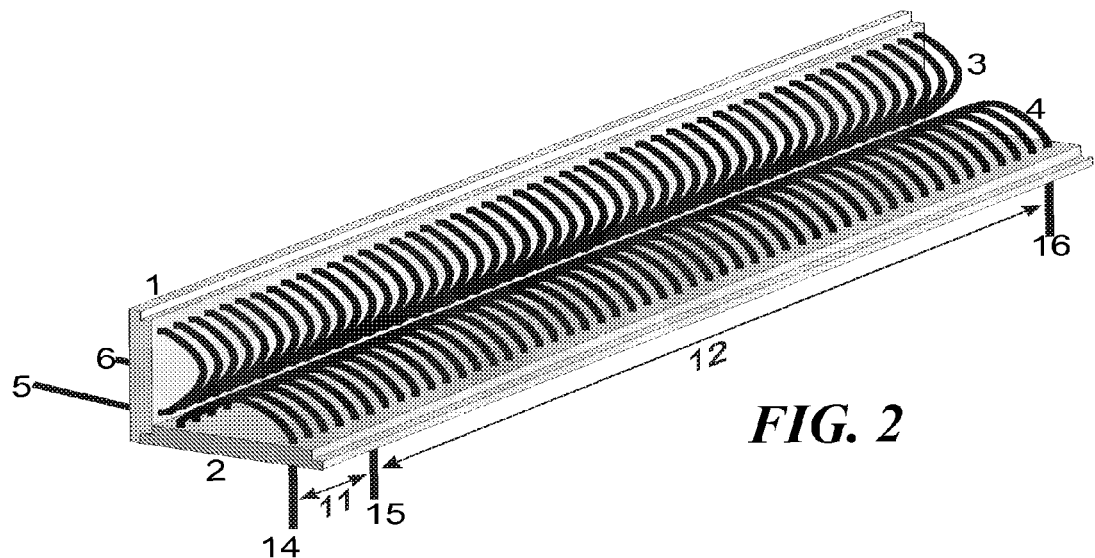
FIG. 2 shows a view into a partially cutaway drift region in which a large number of wire loops (3, 4), which are embedded in the two perforated ceramic plates (1, 2), generate a quadrupole RF field, on which axial DC fields can be superimposed. The ceramic plates (1, 2) have printed circuits on the back, which supply the wires (3, 4) with the DC and AC voltages and, in particular, they have a voltage divider for the DC potentials. The contact pins (5, 6, 14, 15, 16) make it possible to select two different potential gradients for the axial DC fields in the sections (11) and (12) of the drift region.

FIG. 2 shows an embodiment of a drift region which is relatively simple to produce and very useful; in the drawing only two of the four sides of the partially cutaway drift region can be seen. A large number of parallel wire loops (3, 4) are embedded and fastened in the four ceramic plates, of which only ceramic plates (1) and (2) can be seen, which act as the walls of the drift region. The wire loops (3, 4) all have the same hyperbolic shape. They are preferably soldered into electronic circuits printed on the back of the ceramic plates (1, 2). During the soldering, they can be kept in exactly parallel orientation by means of a matrix form. The electronic circuits supply individual RF and DC voltages to the wire loops in such a way that all the wires of one ceramic plate are supplied with the same phase of an RF voltage, but have stepped DC voltages. In the interior, this produces a quadrupole RF field similar to the one in a quadrupole mass filter, which keeps the ions in the axis of the drift region, and a DC potential gradient along the axis.

Although the material is referred to here as "ceramic", it can always be replaced here (and in the following examples) by other insulation materials, for example polyimide. The prerequisite is that these materials have good vacuum resistance and do not contaminate the vacuum by outgassing. It should also be possible to print or vapor-deposit electronic circuits onto the material.

The drift region is preferably divided into two sections (11) and (12) by the contacts (14), (15) and (16) of the ceramic plate (2) (and corresponding contacts in the other ceramic plates). In each of these sections, two separate DC potential gradients can be set by means of voltages across the contacts (14), (15) and (16); the DC potential gradients are easily produced by voltage dividers on the back of the ceramic plates. The contacts (5) and (6) of ceramic plate (1) correspond to the contacts (14) and (15) of ceramic plate (2).

Figure 3:
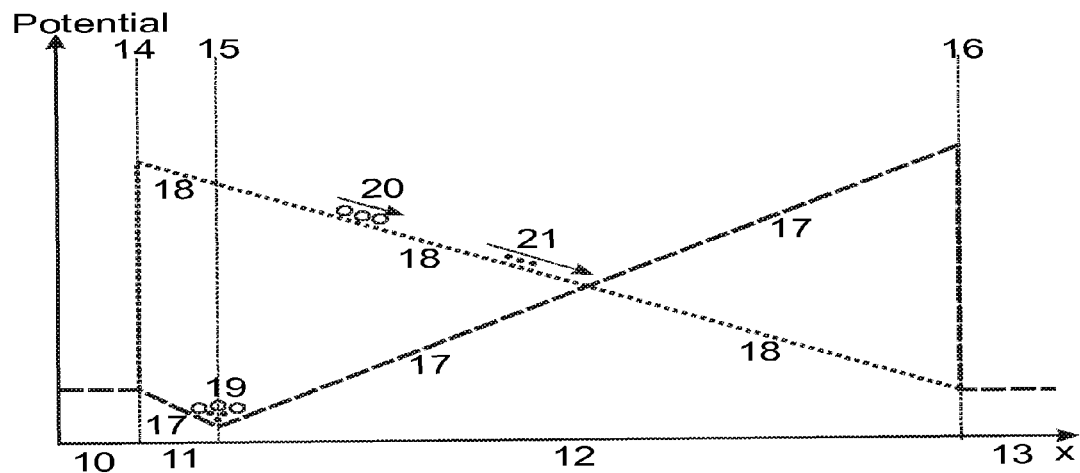
FIG. 3 shows two different potential gradient arrangements (17) and (18) along the sections (11) and (12) of the drift region of FIG. 2. Using the potential gradient arrangement (17), all ions injected from the left are collected in an ion cloud (19) in the potential minimum around the contact pins (6, 15). When the potential gradient arrangement (18) is switched on, the ions start to drift because of their mobility and a separation into slower, more voluminous ions (20) and faster, slimmer ions (21) takes place.

In FIG. 3, the potential profiles (17) and (18) are drawn along the axial direction (x) of sections (11) and (12) for two different operating modes. The potential profile (17) produces a potential minimum in the axial direction in which the different types of ion can collect in the form of an ion cloud (19) during a filling cycle. The ions can enter from the left entrance; this entrance is at a potential which is indicated here in section (10) (without taking lens voltages into consideration). After a sufficient number of ions have collected in the ion cloud (19), the potentials across the contacts (14), (15) and (16) are switched in such a way that the potential profile (18) is now produced. The ions of the ion cloud (19) are now driven through the drift region by the potential gradient of the profile (18), during which they separate into several ion clouds, in this example the two ion clouds (20) and (21), according to their different mobilities and the resulting different drift velocities. These separate ion clouds emerge at different times and, after passing through the ion guide (61) and the second quadrupole mass filter (63), can be measured in the ion detector (65).

Figure 10:
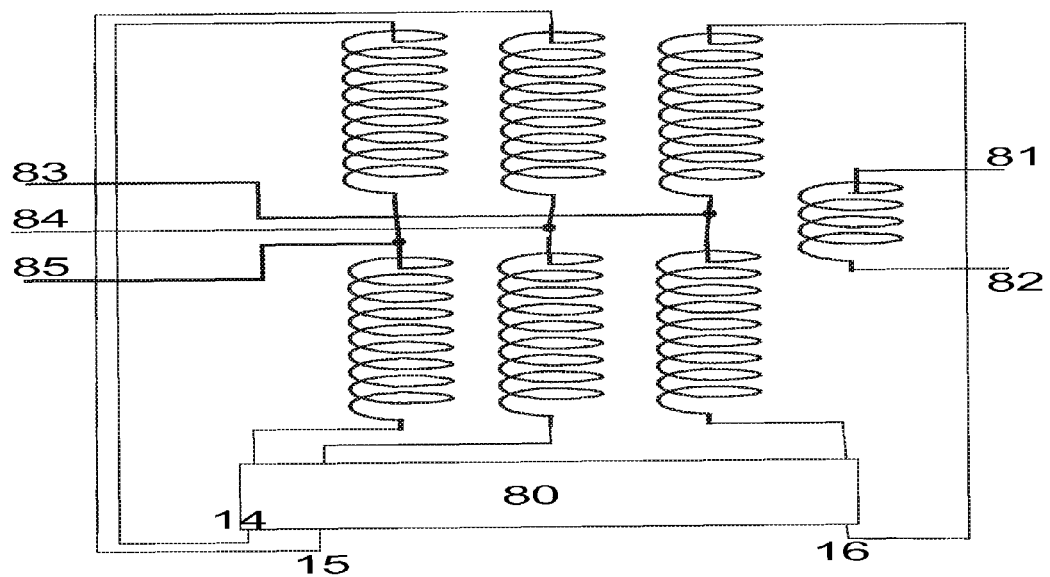
FIG. 10 shows a transformer circuit with three secondary windings which can be used to generate the RF phases and the superimposed DC potentials for a drift region (80) with three inputs (14, 15, 16) (see FIG. 2). The primary winding is supplied via the RF inputs (81, 82); the DC potentials are fed in via the contacts (83, 84, 85).

FIG. 10 shows a transformer circuit with three secondary windings, which can be used to produce the RF voltages with superimposed DC voltage potentials for the contacts (14), (15) and (16) of the arrangement shown in FIG. 2 (and the other contacts). The required DC voltage potentials are fed in via the contacts (83), (84) and (85); contacts (81) and (82) are used to feed the RF voltage into the primary winding.

It should be mentioned here that, because Laplace's equation applies, a potential saddle point must always form in the DC potential minimum for the ion cloud (19). The potential minimum exists only along the axis of the drift region; in the direction radial to this, the electrostatic potential falls off parabolically toward the wire electrodes. This drop needs to be overcompensated by a stronger pseudopotential if ions are to collect here. The strength of the pseudopotential is, however, inversely proportional to the mass-to-charge ratio m/z of the ions. Therefore, only ions of a specific, relatively narrow, mass range can be trapped here. This is not detrimental to the present purpose, however, because, as a rule, the mobilities of ions in only a narrow mass range are to be measured. The mass range of interest normally only covers the ions of one isotopic group. If a mobility spectrum of the ions of a wider mass range has to be measured, it is preferable to collect the ions in the ion guide (57) and then inject them collectively through the lens (58) into the drift region (59).

The wire loop quadrupole arrangement of FIG. 2 is preferably used with stationary collision gas, because a flowing gas suffers perturbations of its laminar motion at the wires, which can lead to turbulences. Turbulences of the collision gas would interfere with the measurement of the ion mobilities. The stationary collision gas is best controlled in a surrounding chamber which is connected with the drift region by only a small number of apertures.

A very similar electrode arrangement can be produced by vapor deposition of thin metal strips transversely across a ceramic plate, with a hyperbolic camber on the plate. In this case, the wires are replaced with thin printed conductors.

As has been elucidated in the Loboda patent (cited above), a collision gas flowing in the opposite direction to the drifting ions can shorten the drift region while having the same effect, or can improve the resolution of the mobility spectrometry for a given drift region length. Therefore, another embodiment uses a drift region that allows better gas guidance and produces a laminar stream with no turbulence.

Figure 4:
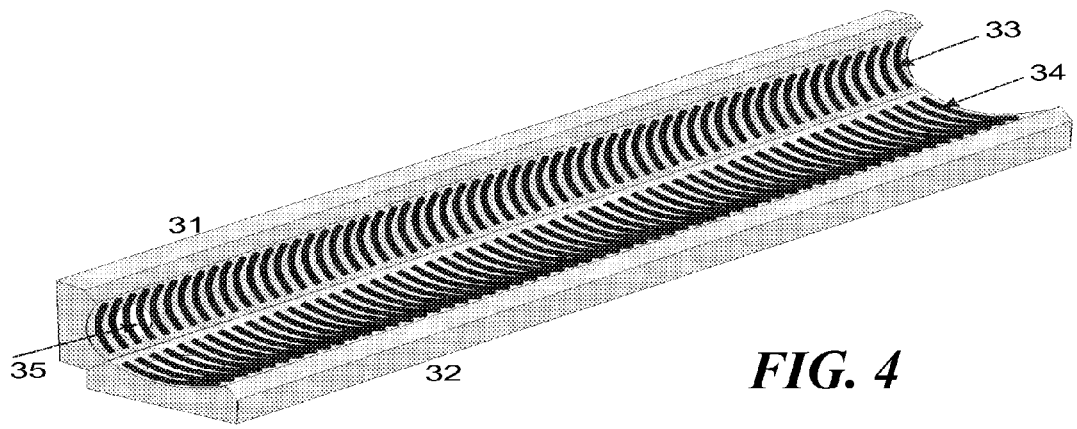
FIG. 4 shows a partially cutaway drift region similar to the one in FIG. 2, but, in this case, with wires (33, 34) which are fitted into the curved sections in two ceramic quadrants (31, 32). A well-defined laminar gas flow can develop in this type of cylindrical drift region. Holes (35) allow the gas fed in from the end to escape. In one configuration, two adjacent wires carrying RF voltages of the same phase, but different amplitudes, create a repulsive pseudopotential directly in front of the wires, while a quadrupole field exists near the axis.
Figure 5:
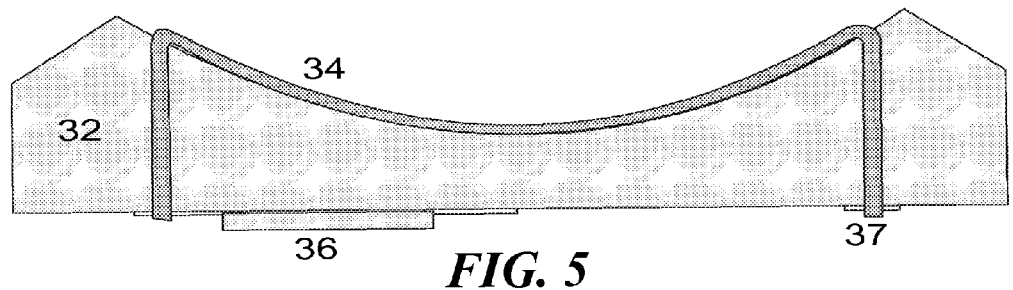
FIG. 5 shows a cross-section of a ceramic quadrant (32), including the embedded wire (34). The electronic resistors and capacitors (36) of a printed circuit are located on the back of the ceramic quadrant (32); the wire (34) is soldered into the printed circuit contact (37).
Figure 6:
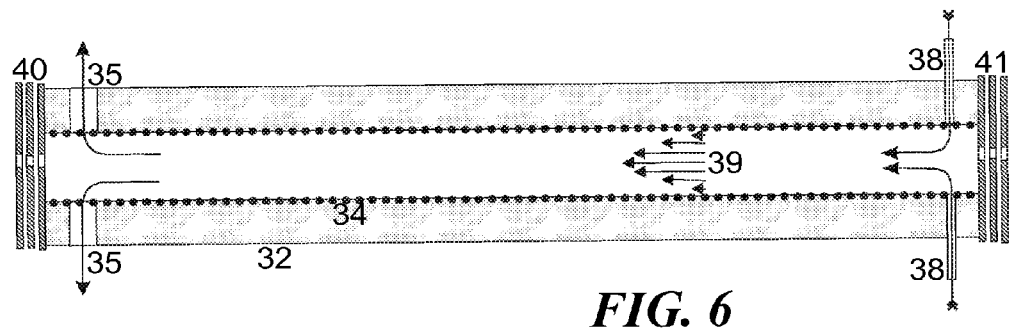
FIG. 6 shows how the gas feeders (38) and exit holes (35) produce a laminar gas flow in the interior with a symbolically indicated parabolic velocity profile (39). The drift region here must be terminated by two lens systems (40, 41) with diaphragm apertures which are as small as possible.

An arrangement of this type is shown in FIGS. 4, 5 and 6. It consists of a hollow ceramic cylinder, in this case consisting of quadrants (31, 32), each equipped with a row of wires on the inside. The wires (33, 34) are arranged parallel to one another and hug the inner curvature of the hollow cylinder. They can be connected up in the same way as the wires in the arrangement in FIG. 2; they then produce a field in the interior which, however, only approaches an ideal quadrupole field close to the axis. Ions are therefore only trapped in the desired way very close to the axis. Those ions which are at a distance from the axis, for example in the middle of the wire curvature, no longer experience a repulsive pseudopotential and can drift to the wires.

A repulsive pseudopotential which acts in the immediate vicinity of the wires can be generated by supplying neighboring wires with RF voltages of the same phase but different amplitudes. (The use of two RF voltages with the same amplitude but slightly different phases is also possible.) The RF dipole voltages which result from the voltage differences between neighboring wires produce a repulsive near-field pseudopotential, which is effective in the vicinity of the wires. By contrast, the RF voltages of the four rows of wire (one row on each quadrant), each averaged over one row of wires, form a quadrupole far-field pseudopotential in the vicinity of the axis, which keeps the ions on axis. By selecting the two amplitudes of the RF voltages across neighboring wires, the near and far fields can be harmonized.

It is also possible to select RF voltages of different frequencies for the generation of the near-field and far-field pseudopotentials.

Here too, the ceramic quadrants (32) can be equipped with electronic circuits (37) on the back, for example by printing or vapor deposition, as is apparent in FIG. 5. The circuits can be equipped with electronic components (36) and allow the wires (34) to be supplied with the desired voltages.

In the interior of this arrangement, a laminar flow of the collision gas can be produced in the cylindrical tube by means of gas inlets (38) and gas exits (35), as is shown in FIG. 6. The collision gas can, of course, also be introduced and removed through slits between the lens systems (41) and (40) and the ceramic tube (32). As is well-known, the laminar flow forms a parabolic profile (39) of the gas velocities. Since the ions are always located precisely in the vicinity of the axis during their drift through the drift region, they always experience the maximum gas velocity on axis, which corresponds exactly to twice the average gas velocity. The radial focusing in the quadrupole field and the resulting uniform velocity of the counter-flowing gas molecules mean that there is no smearing of the ion cloud in addition to the diffusion broadening of the ion cloud. FIG. 6 also shows two lens systems (40) and (41), which transfer the ions from one compartment to the next, at the same time presenting a vacuum barrier for the gas expansion because of their very narrow through-opening.

The drift velocity of the ions can be adjusted via the strength of the potential gradient. Using stationary helium as the collision gas at a pressure of 500 Pascal, a mass-to-charge ratio of approx. 1000 Daltons per elementary charge, and a potential gradient of approx. 100 Volts over a 20 centimeter drift region, results in drift times through the drift region of approx. 10 to 25 milliseconds, depending on the folding of the ions. With a fill time of approx. 5 to 10 milliseconds, measurement of the ion mobility can be repeated approx. 30 times per second.

If one selects a gas velocity close to the drift velocity of the slowest ionic species, this ionic species almost comes to a standstill in the drift region. Ion clouds with similar mobilities can therefore be separated well and their measurement can have a better time resolution. Such gas velocities can be easily produced with an arrangement as shown in FIG. 6.

Figure 7:
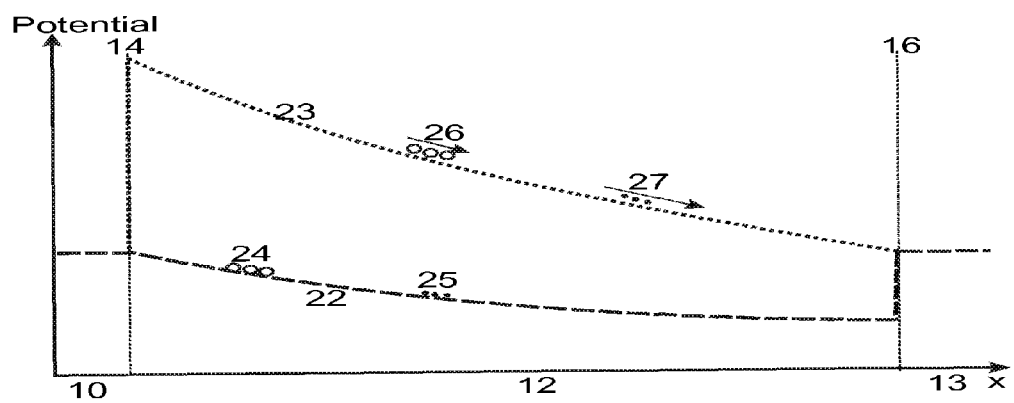
FIG. 7 shows the potential distributions for a particular, stationary mode of operation in a gas flow. A continuously decreasing potential gradient (22) means that introduced ions (24) with a larger collision cross-section are collected at a different point compared to ions (25) with a smaller collision cross-section, because the ions always collect where an equilibrium exists between the decelerating force of the counterflowing gas and the accelerating force of the potential gradient. By switching on the potential characteristic (23), the ions are then fed to a measurement.

This type of drift region with moving gas also permits a second operating mode with an inhomogeneous DC field, as is shown in FIG. 7. This requires adjustment of the voltage divider for the DC potential so that a constant potential gradient is not produced, but rather the DC field is at its maximum at the entrance of the drift region, and continuously decreases though the drift region. This means a different electric field exists at every point in the drift region. If a potential characteristic as shown by the broken line (22) in FIG. 7 is now set, ions introduced with different mobilities collect at different points in the drift region, for example at points (24) and (25), where an equilibrium exists between the electric accelerating force of the electric field and the entraining deceleration force of the moving gas. The ions therefore collect at different points of the drift region and are stationary. They can then be expelled by switching the potential to the profile (23) and measured with temporal resolution. In this case, only two DC voltage potentials need to be applied and switched at the two ends of the drift region.

Instead of the nonlinearly applied potential gradient, it is also possible to use a non-constant, but decreasing, gas velocity, for example by means of a tapered or funnel-shaped tube.

Figure 8:
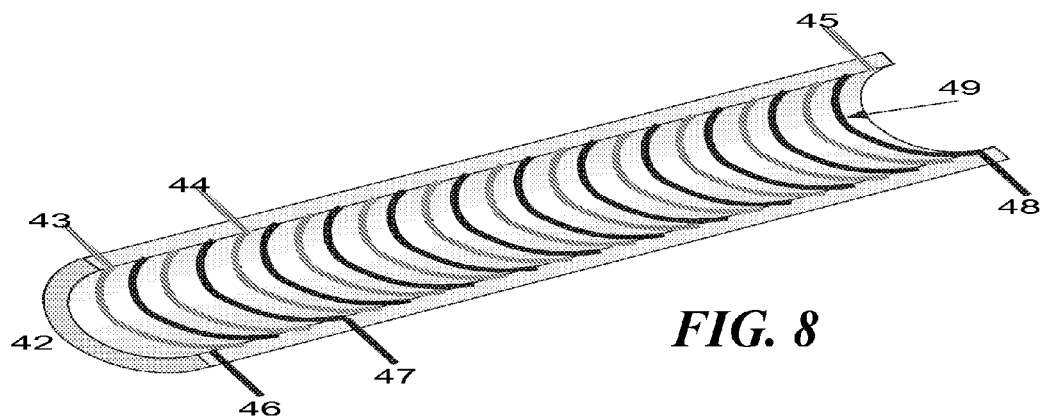
FIG. 8 shows a partially cut-away ceramic tube (42), which contains a double spiral winding (49) of resistance wire (double helix) in the interior, to which the two phases of an RF voltage are connected. This produces a radial pseudopotential which is similar to a quadrupole pseudopotential and keeps ions on axis. The connections (43, 44, 45, 46, 47 and 48) allow DC potential gradients to be generated along the axis by means of the voltage drop across the resistance wire. This arrangement, too, can be used as a drift region with stationary or moving gas.
Figure 9:
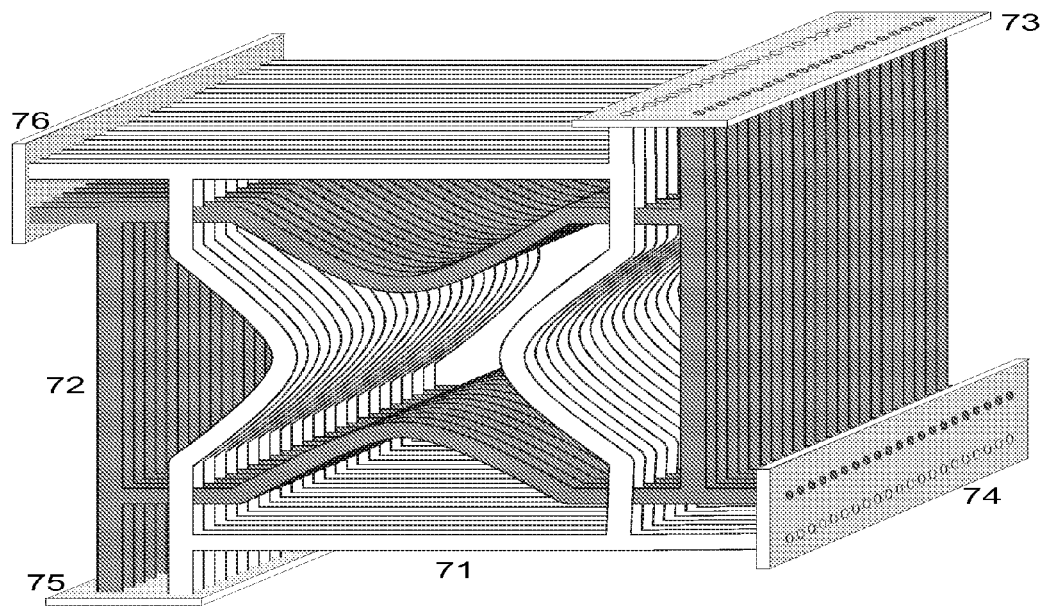
FIG. 9 shows another arrangement which can be used as the drift region: the diaphragm stack comprises diaphragms (71, 72) which are completely identical, but alternately rotated through 90°, across which the two phases of an RF voltage are applied in turn, and also appropriate DC potentials. The supply can be provided via printed circuits on the insulating carrier plates (73, 74, 75, 76).

There are several different embodiments for a drift region which combines a radial focusing by pseudopotentials with a DC electric field acting along the axis, for example a double helix made from resistance wire (FIG. 8), a diaphragm stack made from flat metal plates of a particular shape (FIG. 9), multipole rod systems with an insulated resistance layer, or systems of coaxially arranged ring electrodes, to which alternating phases of an RF voltage are applied (see U.S. Pat. No. 5,572,035 A cited above). These systems will not be discussed further here.

For mobility measurements, the drift region must be filled with a collision gas. For precise measurement of the mobility of analyte ions, it is essential that the collision gas is extremely pure and as inert as possible to avoid the formation of unwanted complex ions during the drift. Pure Helium or Argon are preferred collision gases. Even traces of water $H_2O$ or nitrogen $N_2$ easily result in the attachment of water or nitrogen molecules to some of the analyte ions forming complex ions. Usually, attachment and de-attachment of these molecules oscillate rapidly so that the mobility of an average complex $(M+pH_2O+qN_2)^+$ is measured, p and q being fractional numbers depending on the kind of analyte ion, concentration of the traces, temperature, pressure, and field strength. The arrangement of the invention to sandwich the drift region between two quadrupole mass filters at low pressure helps to keep the collision gas clean. Usually, the analyte ions are generated outside the vacuum system and accompanied on their way into the vacuum system by a large stream of nitrogen. Unavoidably, water molecules penetrate into the vacuum system, too. So the low pressure barrier within the quadrupole mass filters is a big advantage; it helps to avoid penetration of nitrogen and water molecules into the drift region.

If the drift region is equipped with RF-induced pseudopotentials achieving collision focusing of the ions into the axis, then the instrument can be used not only to measure the ion mobility, but also as a triple quadrupole mass spectrometer. These mass spectrometers are used for reliable quantification of chromatographically separated substances by measuring the decomposition of selected parent ions into specific types of daughter ion. The parent ions here are fragmented by collisions in the drift region, if appropriate under a reduced pressure of approximately one Pascal. In this case, the active propulsion of the ions in the axial direction by means of a potential gradient is favorable; it is not usually available in triple quadrupole mass spectrometers.

The gas feeder (68) into the drift region can also be used to introduce mixtures of gases, where one component of the gas can be a reactive gas whose reaction products from reactions with mass-selected ions are to be measured. The instrument is then used as a reaction-product measuring device.

Instead of the detector, an impact plate can be used to collect the ions. Here, it is expedient for an electric deflection unit to deflect the ions of different mobilities to different points on the impact plate. On specially designed surfaces, the ions can be made to land softly by decreasing their kinetic energy, so that they collect in layers. This procedure has become known as "soft landing". The ions collected can subsequently be analyzed further with a mass spectrometer, or they can be used in an investigation of their biological activities. If the kinetic energy is decreased to a lesser degree, the ions can fragment on impact ("crash landing"), making it possible to subsequently measure daughter ions with a mass spectrometer.

The detector and the impact plate can be mounted together on a mobile slide, facilitating a fast exchange.

Persons skilled in the art can easily use this invention as the starting point to develop further application methods and further embodiments. These application methods and embodiments shall be included in this patent protection application.

What is claimed is:

1. A mass spectrometric instrument, comprising, connected in series:
    a) an ion source;
    b) a first mass filter that receives ions from the ion source;
    c) a measuring cell that receives ions from the first mass filter and measures the mobility of the received ions in a collision gas under the influence of an electric field;
    d) a second mass filter that receives ions from the measuring cell; and
    e) an ion detector that directly receives ions from the second mass filter.

2. The mass spectrometric instrument of claim 1, wherein the measuring cell has an axis and comprises electrodes shaped to produce RF-generated pseudopotentials in the measuring cell, which pseudopotentials keep the ions on the axis of the measuring cell.

3. The mass spectrometric instrument of claim 2, wherein the measuring cell further comprises:
    walls fabricated of shaped insulating material;
    wire loops embedded in the insulating material at the inside of the walls; and
    electric circuits that supply RF and DC voltages to the wire loops and are attached to the walls on the outside of the measuring cell.

4. The mass spectrometric instrument of claim 1, wherein the ion detector comprises an impact plate for the collection of the ions.

5. The mass spectrometric instrument of claim 4, further comprising a deflection unit for ions located in front of the impact plate.

6. A method for the analytical investigation of ions with a mass spectrometric instrument having connected in series an ion source, a first mass filter, a measuring cell to measure the mobility of ions in a collision gas under the influence of an electric field, a second mass filter, and an ion detector, the method comprising:
    (a) generating ions in the ion source;
    (b) selecting ions of a predetermined mass range in the first quadrupole filter;
    (c) separating the ions in time by their different mobilities in the measuring cell;
    (d) cleaning the ions of the predetermined mass range from ions of other masses in the second mass filter; and
    (e) measuring the ion currents in the detector as a function of time.

7. The method of claim 6 wherein the measuring cell has a drift region and step (c) comprises filling the drift region with a collision gas in order to measure the mobility of ions.

8. The method of claim 6 wherein the measuring cell has an axis and comprises shaped RF electrodes and wherein step (c) comprises applying RF voltages to the RF electrodes to produce RF-generated pseudopotentials in the measuring cell so that the mass spectrometric instrument functions as a triple quadrupole mass spectrometer for the generation and measurement of fragment ions.

9. The method of claim 8 wherein the measuring cell has a drift region and step (c) comprises filling the drift region with a collision gas having one component that reacts with the ions so that the mass spectrometric instrument functions as a reaction-product mass spectrometer.

10. A cell for measurement of ion mobilities, fragmentation of ions and reaction of ions with reactant gas, the cell having an interior and an exterior and comprising:
    walls fabricated entirely from insulating material and enclosing the cell interior, the walls having a predetermined shape facing the cell interior;
    a plurality of wire loops embedded in the walls; and
    electric circuits that supply RF and DC voltages to the plurality of wire loops and are attached to the walls on the cell exterior.

* * * * *